United States Patent
Fleskes et al.

(10) Patent No.: US 7,273,831 B1
(45) Date of Patent: Sep. 25, 2007

(54) FLORAL PRESERVATIVE AND METHOD OF USE

(76) Inventors: Sharlet Maree Fleskes, 8607 NE. Freemont, Portland, OR (US) 97220; Mark William Fleskes, 8607 NE. Freemont, Portland, OR (US) 97220

( * ) Notice: Subject to any disclaimer, the term of this patent is extended or adjusted under 35 U.S.C. 154(b) by 175 days.

(21) Appl. No.: 11/077,797

(22) Filed: Mar. 10, 2005

(51) Int. Cl.
*A01N 3/02* (2006.01)

(52) U.S. Cl. .............. 504/115; 47/58.1 CF; 47/58.1 R; 47/58.1 FV; 47/58.1 SE; 504/114

(58) Field of Classification Search .......... 47/58.1 CF, 47/58.1 R, 58.1 FV, 58.1 SE, DIG. 11; 504/114, 504/115; 427/4, 425, 458
See application file for complete search history.

(56) References Cited

U.S. PATENT DOCUMENTS

| | | | | | |
|---|---|---|---|---|---|
| 1,489,130 | A | * | 4/1924 | Kropp et al. | 428/22 |
| 1,779,299 | A | * | 10/1930 | Valentine | 427/4 |
| 1,956,908 | A | * | 5/1934 | Neubert | 504/114 |
| 2,013,063 | A | * | 9/1935 | Miller | 427/4 |
| 2,026,873 | A | * | 1/1936 | Dux | 427/4 |
| 2,464,512 | A | * | 3/1949 | Joffe | 427/4 |
| 2,567,929 | A | * | 9/1951 | Fessenden | 427/4 |
| 2,581,299 | A | * | 1/1952 | Rogers | 47/58.1 R |
| 2,614,039 | A | * | 10/1952 | Hamner | 504/115 |
| 2,713,233 | A | * | 7/1955 | Rogers | 47/58.1 R |
| 2,971,292 | A | * | 2/1961 | Maclecki | 47/58.1 R |
| 4,278,715 | A | * | 7/1981 | Romero-Sierra et al. | 428/22 |
| 5,817,600 | A | * | 10/1998 | Carstairs et al. | 504/115 |
| 7,199,082 | B1 | * | 4/2007 | Chapman et al. | 504/115 |
| 2002/0077265 | A1 | * | 6/2002 | Buzzacarini et al. | 510/296 |
| 2002/0086039 | A1 | * | 7/2002 | Lee et al. | 424/401 |
| 2005/0170966 | A1 | * | 8/2005 | Scovell et al. | 504/206 |

OTHER PUBLICATIONS

Anne Post, Feb. 11, 2004, http://web.archive.org/web/20040211071705/http://www.preservedgardens.com/flower-dye.htm.*

* cited by examiner

*Primary Examiner*—Teri Pham Luu
*Assistant Examiner*—Valentina Xavier
(74) *Attorney, Agent, or Firm*—Mark S. Hubert

(57) ABSTRACT

This invention is a new floral preservative that utilizes a novel formulation of using a combination of known and readily available over the counter products that, when sprayed onto the flower as directed, approximately doubles the vase life of fresh cut flowers or preserves flowers to a pliable, non crumbly state approximating their naturally vibrant colors. It is applied to the exterior of the fresh cut flowers in a misting apparatus, therein simplifying the art of preserving flowers.

7 Claims, 3 Drawing Sheets

FLORAL PRESERVATIVE AND METHOD OF USE

BACKGROUND OF THE INVENTION

Across the past three years, retail sales of floral products in the United States have remained nearly unchanged at approximately $13 billion. In the past, fresh-cut flowers have dominated the floral product market, but trends are changing. The sales of dried flowers has drastically increased. This is for a good reason. With the rising cost of fresh cut flowers, consumers want more than a few days of visual enjoyment for their hard earned money. Similarly, retailers don't want to be caught with hoards of wilted flowers in their inventory. The present invention relates to a floral preservative, and more particularly, to a chemical spray that may be utilized in conjunction with fresh cut flowers to prolong and enhance their beauty, and also having the capability of preparing them for use as preserved, vibrantly colored, pliable dried flowers.

Fresh cut flowers begin to loose their freshness as soon as they are cut. Despite attempts to lengthen their lifetime, their leaves and petals wilt and discolor until they are no longer aesthetic affable enough to continue displaying. Considering the cost of certain floral species, this is an undesirable situation. The existing preservatives focus on the fact that cut flowers mainly absorb water from their cuts, and consequently try to prolong the flowers vase life by submersing the cut stem region in water containing a concentrated, powdered or tablet preservative. Unfortunately, these preservatives adjust the pH of the water and create an environmental waste to be dealt with.

Fresh cut flowers, rather than being displayed immediately, may be prepared for use as a preserved or "dried" flower. While dried flowers eliminate the abovementioned problem of wilting as well as molding, they have three inherent problems: they shrink about ten percent; they are fragile, often crumbling to the touch; and, they lack the intensity or vibrance of the flower's original color. This is a function of they way that they have been preserved.

Traditionally, dried flowers have been hung upside down in a dark, dry or desiccated environment to remove the flower's stored water. Often their water stores are replaced by soaking the cut stems with glycerin mixed with food dyes/coloring prior to drying.

Thus, it can be seen that the norm for enhancing dried or fresh cut floral arrangements has been an internal process wherein the flower draws fluid up the stem.

This new floral preservative utilizes a novel formulation that, when sprayed onto the flower as directed, approximately doubles the vase life of fresh cut flowers or preserves flowers to a pliable, non crumbly state approximating their natural vibrance therein overcoming the abovementioned drawbacks.

SUMMARY OF THE INVENTION

In accordance with the invention, an object of the present invention is to provide an improved floral preservative and method of use that does not pollute the environment or leave the flower in a pale, fragile state.

The general purpose of the present invention, which will be described subsequently in greater detail, is to provide a new floral preservative that creates a pliable, colorful dried flower which is not anticipated, rendered obvious, suggested, or even implied by any of the prior art, either alone or in any combination thereof.

It is another object of this invention to provide a spray floral preservative that can be used to either enhance the vase life of fresh cut flowers or to preserve fresh cut flowers in the most life like condition possible.

It is a further object of this invention to provide a simple chemical solution and method for preserving flowers. This is accomplished using a combination of known and readily available over the counter products.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements. Other objects, features and aspects of the present invention are discussed in greater detail below.

DETAILED DESCRIPTION

Figure 1:
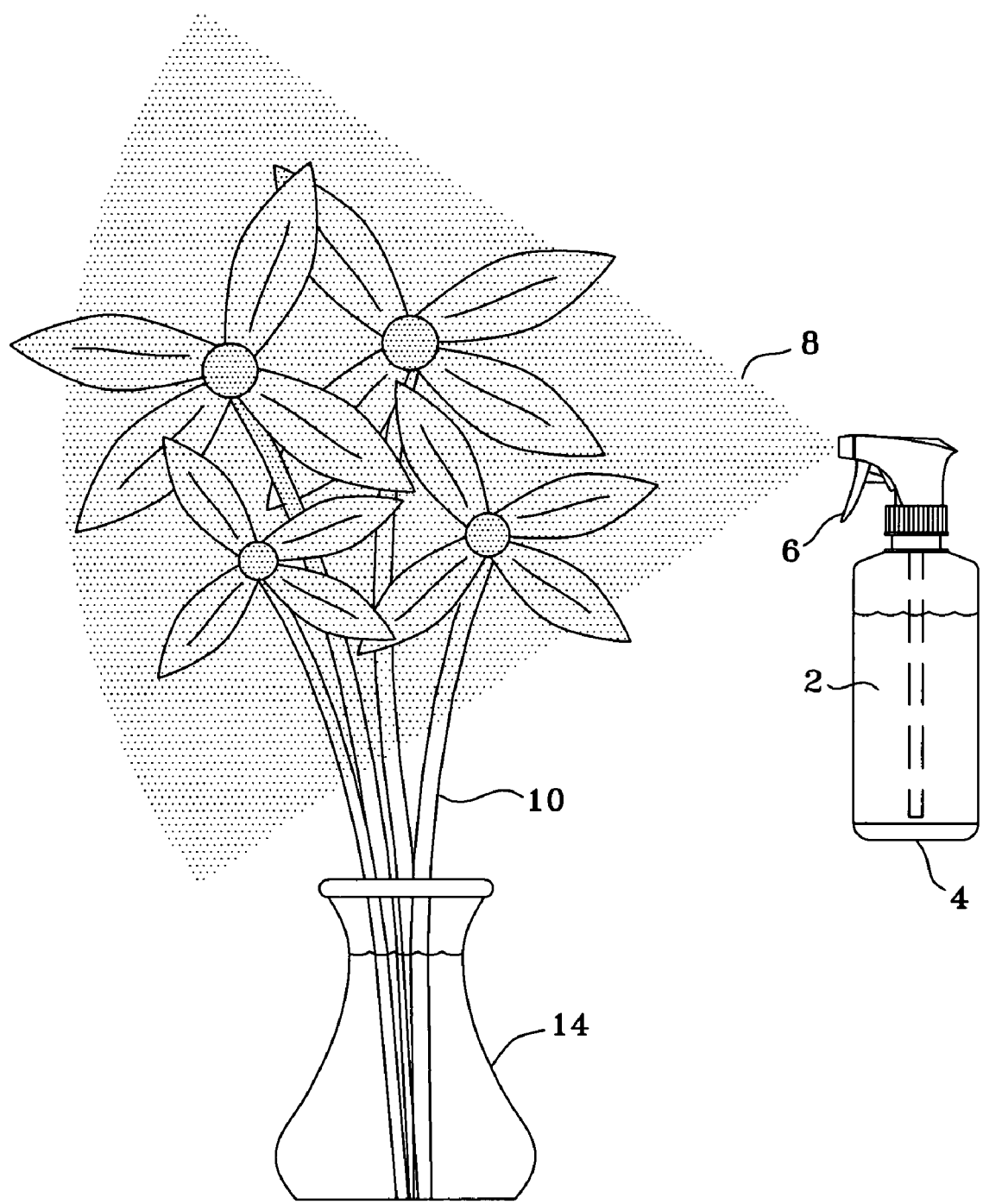
FIG. 1 is a side view of the floral preservative being misted onto fresh cut vase flowers.

The floral preservative of the present invention, is comprised of a mixture of commonly available, over the counter household ingredients. When the appropriate proportions of these ingredients are mixed in the described manner, it results in an opaque, pink liquid solution with the consistency of milk. This liquid solution is applied to the exposed surfaces of prepared flowers by a misting applicator until the flower is coated and dripping. After each application the flower is then suspended upside down and allowed to partially dry in a dark, ventilated environment. This process is repeated daily for three days, then allowed approximately two weeks to completely dry. The petals and leaves of the resultant preserved flower (commonly called "dried") will have be supple and pliable such that when touched will not flake or crumble. The coloration of the flower will be slightly less than the original yet still vibrant and will resist fading. Mold and mildew on the flower surfaces will be inhibited.

The floral preservative is comprised of the following, commercially available, over-the-counter ingredients:

A liquid fabric softener from any of the common proprietary formulations adapted for softening or conditioning fabrics in the wash cycle of an automatic washing machine by imparting a durably increased capacity of water absorption (hydrophilicity) and a durably decreased susceptibility to accumulation of static electricity to textile fibre materials. These are commonly of the cationic softener type;

A liquid laundry starch for ironing which is generally an aqueous cornstarch solution with proprietary ingredients such as borax, processing aids, preservatives, ironing aids, and perfume;

A pectin based product for jelling fluid foodstuffs. These are generally a powdered mixture of fruit pectin, Dextrose, and Fumaric Acid adapted for making jams, jellies, custards, candies and the like;

A white, polyvinyl based liquid glue adhesive for multi purpose household use;

A liquid laundry bluing adapted to impart a slight blue hue to fabrics to enhance the brightness of the white component. These are generally a powdered blue iron in a colloidal suspension with a pH balancer and a biocide; and A whitener and brightener dye that is adapted for coloring fabric and clothing. These generally contain Sodium Hydrosulfite, Sodium Carbonate Anhydrous, Sodium Chloride and optical brighteners.

It has been demonstrated, albeit through limited experimentation, that the variance in the ingredients and additives employed by specific product manufacturers of the aforementioned commonly available commercial products is not critical to the performance of the floral preservative.

Floral-Preservative Formulation

The following table describes the chemical components and their volumes or weights that are necessary to make up 5 US gallons (640 fl oz) of the floral preservative. Since many of the formulations are proprietary the composition as disclosed publically is all that is listed.

| Common Name as per MSDS and TM Registration | Composition | Amount & Approx wt % | Trade Name |
|---|---|---|---|
| pink liquid fabric softener | cationics and fragrance | 144 fl oz (4.25 l) (4,250 g) 23.48% | Home Best Fabric Softener Rinse |
| liquid laundry starch | water, cornstarch, Borax, processing aids, preservative, ironing aid, perfume | 48 fl oz (1.42 l) (1,448.4 g) 8.00% | Dial "Sta-Flo" concentrated Liquid Starch |
| white cane sugar | $C_{12}H_{22}O_{11}$ | 29 wt oz (803 g) 4.43% | Care |
| white liquid glue | polyvinyl acetate (PVA) resin emulsion | 64 fl oz (1.90 l) (68.5 g) .37% | Elmer's Glue - All (PVAC based adhesive) |
| liquid bluing | powdered blue iron in a colloidal suspension with a pH balancer and a biocide | 1 fl oz (29.6 ml) (29.6 g) .16% | Ms. Stewart's Concentrated Liquid Bluing |
| liquid whitener and brightener | Sodium Hydrosulfite, Sodium Carbonate Anhydrous, Sodium Chloride, Optical Brighteners | 1 fl oz (29.6 ml) (29.6 g) .16% | Rit Whitener and Brightener |
| pectin | Dextrose, Fumaric Acid Fruit Pectin. | 4 wt oz (112 g) .62% | Kraft "Sure Jell" Fruit Pectin |
| Distilled Water | $H_2O$ | 384 fl oz (11,356 g) 62.75% | |

Floral Preservative Preparation

To make 11,356 g (approximately 5 gallons) of the floral preservative, the abovementioned ingredients are combined in the following manner:

1. Dissolve 4 wt oz (112 g) pectin and 29 wt oz (803 g) sugar in 64 fl oz of room temperature distilled water.
2. Add 144 fl oz (4.25 l) pink fabric softener and mix until homogeneous.
3. Add 48 fl oz (1.42 l) liquid starch and mix until homogeneous.
4. Add 64 fl oz (1.90 l) glue and mix until homogeneous.
5. Add 1 fl oz (29.6 ml) liquid whitener and mix until homogeneous.
6. Add 1 fl oz (29.6 ml) liquid bluing and enough water to bring mixture to 640 fl oz (approximately 360 to 390 fl oz of water) and mix until homogeneous.

The floral preservative works through the synergistic cumulation of the various properties imparted by the various components. The fabric softener penetrates the surface and it's positively charged nitrogen atoms bond to the plant's negatively charged molecules, imparting the flexibilty and soft feel to the flowers and petals as well as reducing petal creases and wrinkles, making the petals smoother. The starch maintains the rigidity of the stem and supporting foliage. The sugar aids in the absorption of the floral preservative into the flower petals so as to keep the petals plumper that those of traditionally dried flowers. It also adds a slight sheen to the surface finish. The glue acts as a media to bind a thicker coat of the floral preservative to the flower's surface and to seal pores. It also dries clear. The bluing prevents the petals from yellowing/browning enhances the white colors and retards the growth of algae, bacteria, mold and mildew on the flower surfaces. The whitener brightens all colors. The pectin solidifies any remaining moisture in the flower, keeps the petals from drooping and keeps the stem rigid. Water is essentially a carrier and mixture agent for the above materials and a gelling substrate for the pectin.

The floral preservative must always be used with fresh cut flowers. It is best to always use within the first twelve hours of cutting the stems. It may be used to enhance and extend the vase life of displayed fresh cut flowers or to preserve fresh cut flowers for use in a preserved or "dried" flower arrangement.

Referring to FIG. 1, the floral preservative 2 can be seen in spray mist applicator 4. To enhance and extend the vase life of displayed fresh cut flowers 10 in vase 14, pump head 6 is manipulated to generate mist 8 at a distance of approximately four to six inches from the exposed portions of flowers 10. Floral preservative 2 is sprayed liberally over the flowers 10, until they are dripping slightly. This must be done particularly in the blossom and petal regions once flowers 10 have begun to open. It may be sprayed on flowers 10 daily but every three days is all that is required. The vase life should be approximately doubled.

Figure 2:
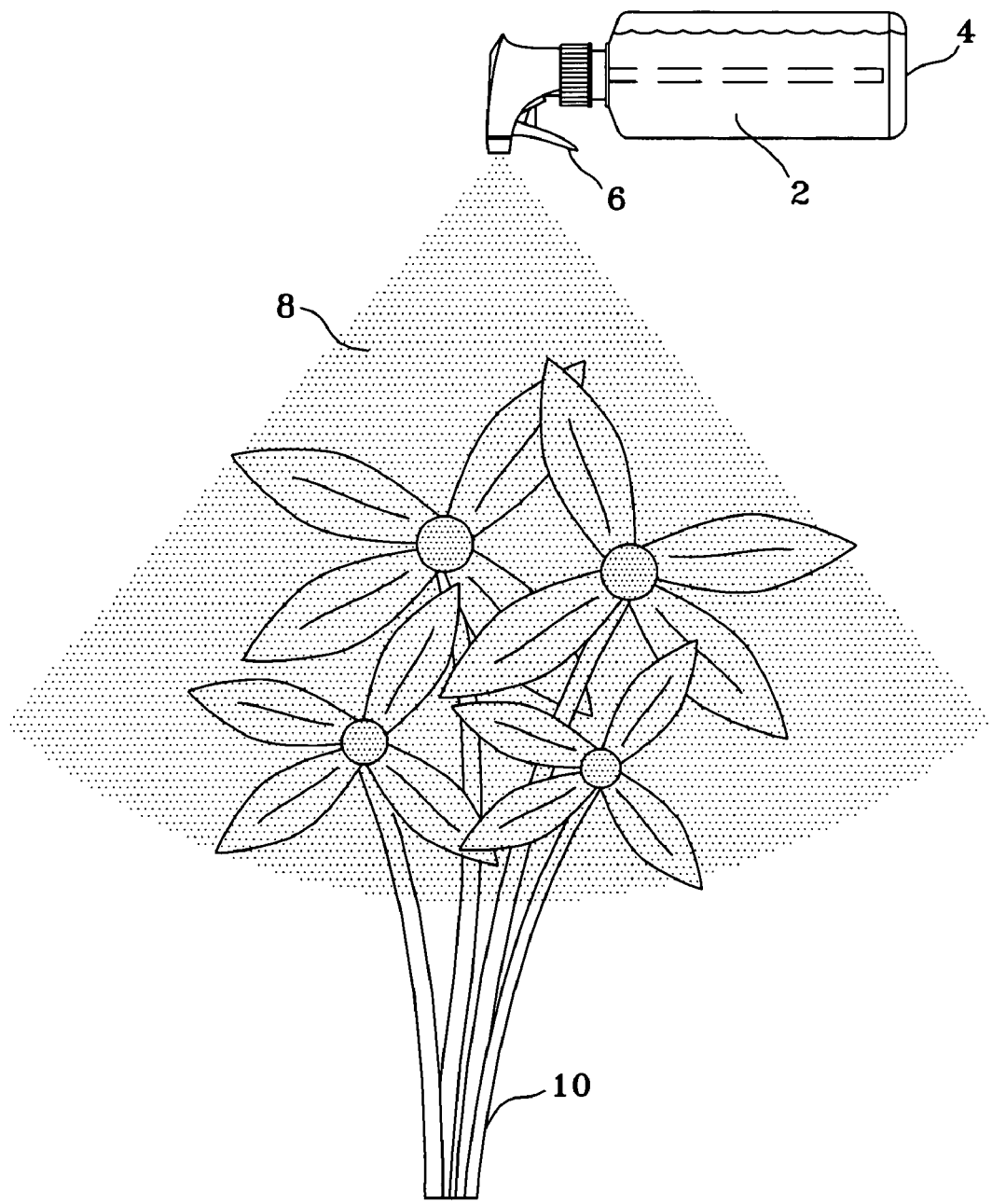
FIG. 2 is a side view of the floral preservative being misted into the blossoms of fresh cut flowers for preservation prior to their hanging.
Figure 3:
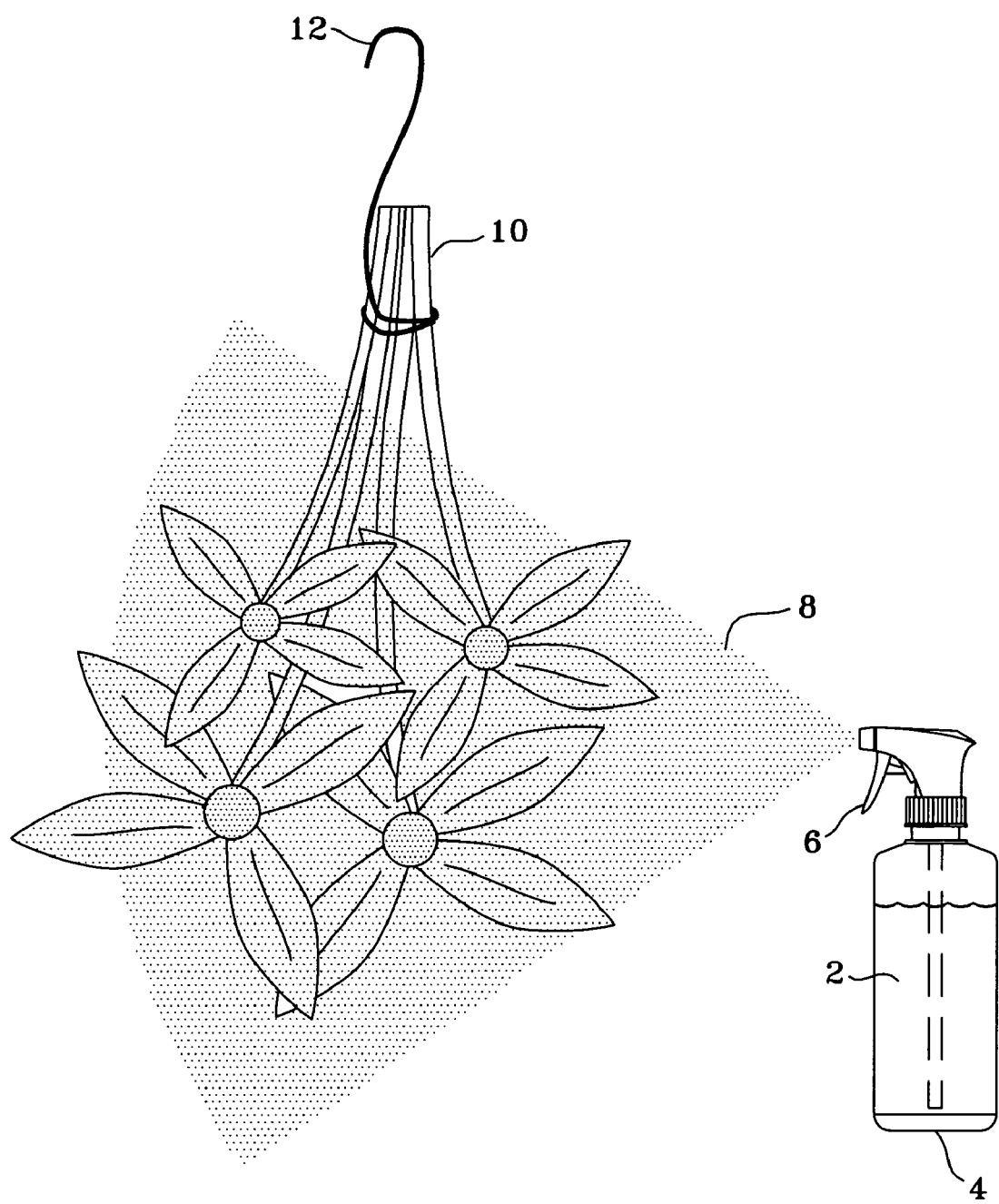
FIG. 3 is a side view of the floral preservative being misted onto hanging, partially preserved flowers.

Referring to FIG. 2 and FIG. 3, while referring to the steps of the following method best illustrate how to use floral preservative 2 for preserving fresh cut flowers 10 for later, possibly permanent use in preserved arrangements Step 1. Begin with fresh cut flowers in a fully hydrated state. Shake floral preservative 2 well before use.

Step 2. Clean and remove any brown, dead or drying leaves. Rinse flowers 10 with water, gently shaking off the extra.

Step 3. Holding flowers 10 upright by stem, manipulate pump head 6 to generate mist 8 approximately between four to six inches from flowers 10. Shoot mist directly into the center of the flowers 16 and the stem 18 until floral preservative 2 is dripping from the flowers 10. Turn flowers 10 upside down and spray underside until floral preservative 2 is again dripping.

Step 4. Tightly wrap a fine wire 12 around the stem grouping. Hang bloom end down in a dark warm place to dry.

Step 5. For the next three days repeat Step 3. Allow up to two weeks to fully dry.

Following the aforementioned method should result in pliable, crumble resistant, preserved flowers retaining much of their original color and luster that will resist mold or mildew and not discolor.

When cleaning dust or surface particulate from the flowers 10 through the years of enjoyment that they will bring, the flower 10 is to be misted with natural water and a single coat of the floral preservative 2.

The above description will enable any person skilled in the art to make and use this invention. It also sets forth the best modes for carrying out this invention. There are numerous variations and modifications thereof that will also remain readily apparent to others skilled in the art, now that the general principles of the present invention have been disclosed. Although the formulae disclosed above refers to brand name ingredients, experimentation has shown that brand loyalty is not critical and that most commercially available equivalent products will achieve the same results.

What is claimed is:

1. A floral preservative surface misting solution comprising:
   pink liquid softener comprises between about 3.83 Liters to 4.48 liters of the solution;
   liquid laundry starch comprises between about 1.28 Liters to 1.56 liters of the solution;
   white cane sugar comprises between about 722 grams to 883 grams of the solution; said white liquid glue comprises between about 1.71 liters to 2.09 Liters of the solution;
   liquid bluing comprises between about 26 milliliters to 32 milliliters of the solution;
   liquid whitener and brightener comprises between about 26 milliliters to 32 milliliters of the solution;
   pectin comprising between about 100 grams to 123 grams of the solution; and
   water.

2. The floral preservative of claim one wherein all components are commercially available products and further, wherein;
   said pink liquid softener is selected from one of the common pink liquid softener proprietary formulations adapted for softening or conditioning fabrics in the wash cycle of an automatic washing machine by imparting a durably increased capacity of water absorption;
   said liquid laundry starch is selected from one of the common liquid laundry starch aqueous cornstarch base proprietary formulations adapted for ironing;
   said white liquid glue is selected from one of the common proprietary white liquid glue formulations of polyvinyl based liquid glue adhesives adapted for multi purpose household use;
   said liquid bluing is selected from one of the common liquid bluing proprietary formulations of concentrated bluing adapted to impart a slight blue hue to fabrics to enhance the brightness of the white component;
   said liquid whitener and brightener dye is selected from one of the common proprietary liquid whitener and brightener formulations of fabric dyes adapted for coloring fabric and clothing;
   said pectin is selected from one of the common proprietary formulations of fruit pectin adapted for making jams, jellies, custards, candies and the like; and
   said water is distilled.

3. A floral preservative surface misting solution comprising:
   approximately 23.48% by weight pink liquid softener + or −10%;
   approximately 8.00% by weight liquid laundry starch + or −10%;
   approximately 4.43% by weight white cane sugar + or −10%;
   approximately 0.37% by weight white liquid glue + or −10%;
   approximately 0.16% by weight liquid bluing + or −10%;
   approximately 0.16% by weight liquid whitener and brightener + or −10%;
   approximately 0.62% by weight pectin + or −100%; and
   the balance of said solution is water.

4. A floral preservative surface misting solution comprising:
   approximately 23.48% by weight pink liquid softener + or −10%;
   approximately 8.00% by weight liquid laundry starch + or −10%;
   approximately 4.43% by weight white cane sugar + or −10%;
   approximately 0.37% by weight white liquid glue + or −10%;
   approximately 0.16% by weight liquid bluing + or −10%;
   approximately 0.16% by weight liquid whitener and brightener + or −10%;
   approximately 0.62% by weight pectin + or −10%; and
   the balance of said solution is water;
   wherein said pink liquid softener is selected from one of the common pink liquid softener proprietary formulations adapted for softening or conditioning fabrics in the wash cycle of an automatic washing machine by imparting a durably increased capacity of water absorption;
   said liquid laundry starch is selected from one of the common liquid laundry starch aqueous cornstarch base proprietary formulations adapted for ironing;
   said white liquid glue is selected from one of the common proprietary white glue formulations of polyvinyl based liquid glue adhesive adapted for multi purpose household use;
   said liquid bluing is selected from one of the common liquid bluing proprietary formulations of concentrated bluing adapted to impart a slight blue hue to fabrics to enhance the brightness of the white component;
   said liquid whitener and brightener dye is selected from one of the common proprietary liquid whitener and brightener formulations of fabric dyes adapted for coloring fabric and clothing;
   said pectin is selected from one of the common proprietary formulations of fruit pectin adapted for making jams, jellies, custards, candies and the like; and
   said water is distilled.

5. A floral preservative surface misting solution comprising:
   approximately 23.48% by weight pink liquid softener;
   approximately 8.00% by weight liquid laundry starch;
   approximately 4.43% by weight white cane sugar;
   approximately 0.37% by weight white liquid glue;
   approximately 0.16% by weight liquid bluing;
   approximately 0.16% by weight liquid whitener and brightener;
   approximately 0.62% by weight pectin; and
   the balance of said solution is water.

6. A floral preservative surface misting solution comprising:
   approximately 23.48% by weight pink liquid softener;
   approximately 8.00% by weight liquid laundry starch;
   approximately 4.43% by weight white cane sugar;
   approximately 0.37% by weight white liquid glue;
   approximately 0.16% by weight liquid bluing;
   approximately 0.16% by weight liquid whitener and brightener;
   approximately 0.62% by weight pectin; and the balance of said solution is water;

wherein said pink liquid softener is selected from one of the common pink liquid softener proprietary formulations adapted for softening or conditioning fabrics in the wash cycle of an automatic washing machine by imparting a durably increased capacity of water absorption;

said liquid laundry starch is selected from one of the common liquid laundry starch aqueous cornstarch base proprietary formulations adapted for ironing;

said white liquid glue is selected from one of the common proprietary white glue formulations of polyvinyl based liquid glue adhesive adapted for multi purpose household use;

said liquid bluing is selected from one of the common liquid bluing proprietary formulations of concentrated bluing adapted to impart a slight blue hue to fabrics to enhance the brightness of the white component;

said liquid whitener and brightener dye is selected from one of the common proprietary liquid whitener and brightener formulations of fabric dyes adapted for coloring fabric and clothing;

said pectin is selected from one of the common proprietary formulations of fruit pectin adapted for making jams, jellies, custards, candies and the like; and said water is distilled.

7. The method of using a floral preservative surface misting solution to preserve fresh cut flowers comprising the following steps:

applying a mist of said solution approximately between four to six inches from flowers held upright by stem, directing said mist into the center of the flowers and the stem until said solution is dripping from the flowers, turning flowers upside down and applying a mist to the underside until solution is again dripping, hanging flowers bloom end down in a dark warm place to dry by a wire wrapped tightly around the stems, Repeat for the next three days and allow up to two weeks to fully dry, wherein said solution is made from:

approximately 23.48% by weight pink liquid softener;

approximately 8.00% by weight liquid laundry starch;

approximately 4.43% by weight white cane sugar;

approximately 0.37% by weight white liquid glue;

approximately 0.16% by weight liquid bluing;

approximately 0.16% by weight liquid whitener and brightener;

approximately 0.62% by weight pectin; and the balance of said solution is water.

* * * * *